United States Patent
Yonce et al.

(10) Patent No.: US 7,917,212 B2
(45) Date of Patent: Mar. 29, 2011

(54) EMI DETECTION FOR IMPLANTABLE MEDICAL DEVICES

(75) Inventors: David J. Yonce, Fridley, MN (US); Luke Babler, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 979 days.

(21) Appl. No.: 11/752,385

(22) Filed: May 23, 2007

(65) Prior Publication Data

US 2007/0219594 A1 Sep. 20, 2007

Related U.S. Application Data

(63) Continuation of application No. 10/642,068, filed on Aug. 14, 2003, now Pat. No. 7,231,251.

(51) Int. Cl.
*A61N 1/372* (2006.01)
(52) U.S. Cl. .......................................................... 607/9
(58) Field of Classification Search ............... 607/9, 27, 607/32, 60; 128/901
See application file for complete search history.

(56) References Cited

U.S. PATENT DOCUMENTS

| | | | |
|---|---|---|---|
| 5,217,010 A | 6/1993 | Tsitilk et al. | |
| 5,438,990 A | 8/1995 | Wahlstrand et al. | |
| 5,629,622 A | 5/1997 | Scampini | |
| 5,649,965 A | 7/1997 | Pons et al. | |
| 5,662,694 A | 9/1997 | Lidman et al. | |
| 5,697,958 A * | 12/1997 | Paul et al. | 607/31 |
| 5,722,998 A | 3/1998 | Prutchi et al. | |
| 5,766,227 A | 6/1998 | Nappholz et al. | |
| 5,817,136 A | 10/1998 | Nappholz et al. | |
| 6,101,417 A | 8/2000 | Vogel et al. | |
| 6,188,926 B1 | 2/2001 | Vock | |
| 6,778,856 B2 | 8/2004 | Connelly et al. | |
| 6,788,973 B2 | 9/2004 | Davis et al. | |
| 6,937,906 B2 | 8/2005 | Terry et al. | |
| 6,954,674 B2 | 10/2005 | Connelly | |
| 7,076,283 B2 | 7/2006 | Cho et al. | |
| 7,082,328 B2 | 7/2006 | Funke | |

* cited by examiner

*Primary Examiner* — George R Evanisko
(74) *Attorney, Agent, or Firm* — Schwegman, Lundberg & Woessner, P.A.

(57) ABSTRACT

A method and system for the detection of electromagnetic interference is disclosed in which a telemetry coil or other magnetic sensor is used to detect a magnetic signal. If a magnetic signal is determined to be a non-telemetry signal and is time-correlated with the onset of an increase in heart rate, electromagnetic interference is assumed to be present.

20 Claims, 5 Drawing Sheets

EMI DETECTION FOR IMPLANTABLE MEDICAL DEVICES

CROSS-REFERENCE TO RELATED APPLICATIONS

This application is a continuation of U.S. patent application Ser. No. 10/642,068, filed on Aug. 14, 2003 now U.S. Pat. No. 7,231,251, the specification of which is incorporated herein by reference.

FIELD OF THE INVENTION

This invention pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate all of the above functionalities.

Cardiac rhythm management devices such as described above monitor the electrical activity of heart via one or more sensing channels so that pacing pulses or defibrillation shocks can be delivered appropriately. Such sensing channels are made up of implanted leads which have electrodes disposed internally near the heart, which leads may also be used for delivering pacing pulses or defibrillation shocks. Such implanted leads, however, may also act as antennas for extraneous electromagnetic fields, referred to as electromagnetic interference (EMI). For example, theft prevention systems commonly employ high-strength magnetic fields to detect the presence of a magnetic tag placed on retail merchandise. Most of these systems modulate or pulse the magnetic field in such a way that the repetition rate falls within the passband of cardiac sensing amplifiers. When these fields are coupled to the implanted leads of a cardiac rhythm management device, signals are produced in the device's sensing channels which may be misinterpreted as cardiac electrical activity, thus causing inappropriate inhibition of pacing and/or inappropriate delivery of defibrillation shocks.

SUMMARY

The present invention is a method and system by which an implantable cardiac rhythm management device may detect the presence of EMI. In accordance with the invention, EMI is detected by using a magnetic sensor incorporated into the device. Such a sensor may be a dedicated device or may be the telemetry coil which is normally used by the device to send and receive telemetry communications via an inductive link. The device detects EMI by detecting the presence of a magnetic signal with the magnetic sensor, distinguishing the magnetic signal from a telemetry communication, and time correlating the onset of the magnetic signal with detection of increased intrinsic cardiac activity over the device's sensing channels. The device may then be programmed to enter a noise reversion mode in which inhibition of pacing and/or delivery of defibrillation shocks are prevented while the EMI is present.

DETAILED DESCRIPTION

Figure 1:
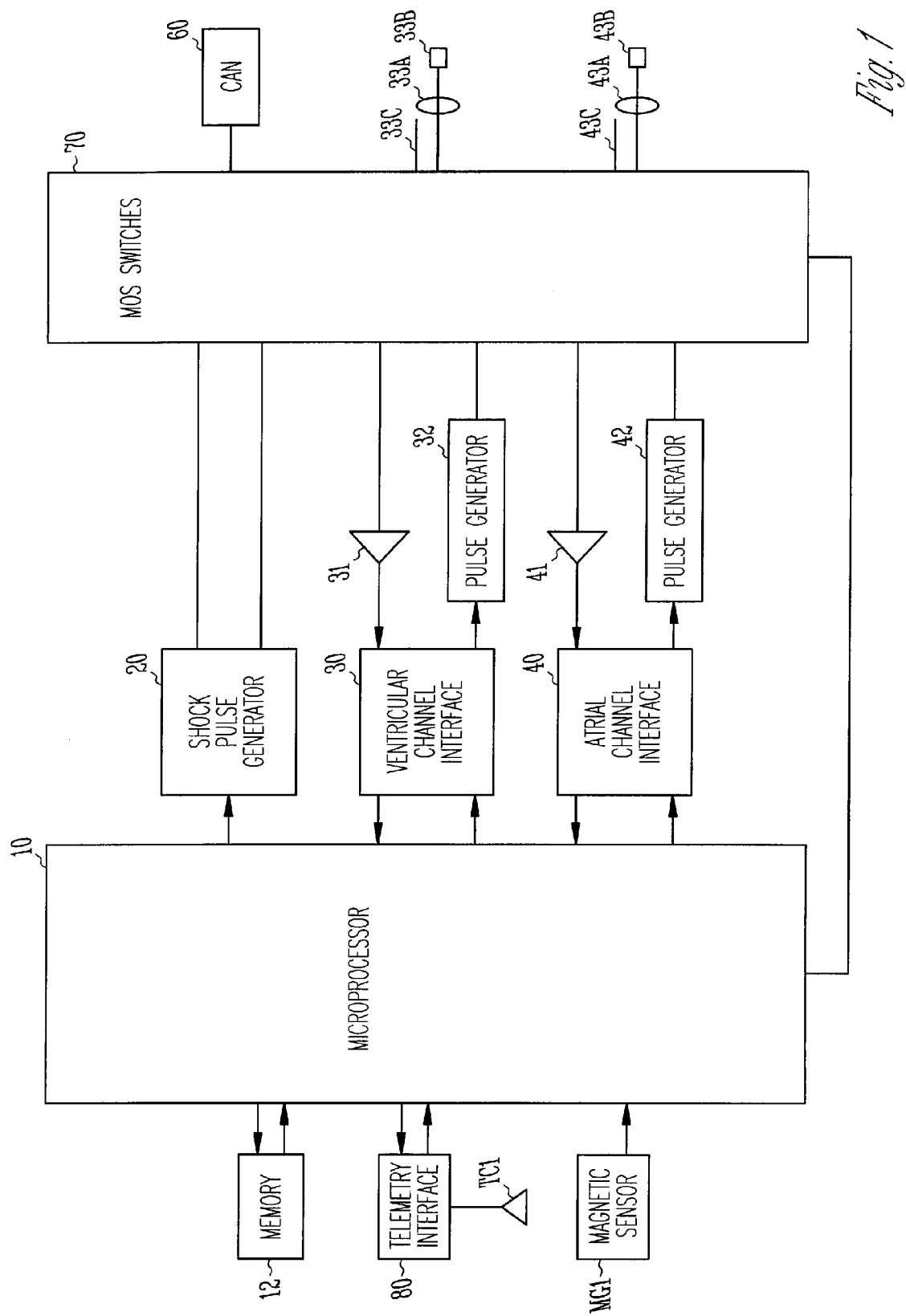
FIG. 1 is a block diagram of an exemplary cardiac rhythm management device for practicing the present invention.

As noted above, EMI from various sources may interfere with the ability of an implanted cardiac rhythm management device to deliver appropriate therapy. One approach to the problem of detecting EMI is exemplified by U.S. Pat. No. 5,697,958 (referred to as the '958 patent), assigned to Cardiac Pacemakers Inc., and hereby incorporated by reference. The '958 patent discloses an implantable device which has dedicated signal processing circuitry for filtering a signal generated by a telemetry coil or other sensing means in accordance with the characteristics expected of external noise. A signal representative of the noise is thereby derived, and its amplitude is then compared with a specified threshold value to determine if EMI is present. Upon detection of EMI, the device may be configured to take various actions, including initiation of a noise reversion mode.

The approach of the present invention to the problem of EMI detection is different from that of the '958 patent. A signal proportional to any time-varying magnetic field which may be present is generated by either a telemetry coil or a dedicated magnetic sensor, and a check is made to see if the magnetic signal may be due to a telemetry transmission. If not, the signal is deemed to be a non-telemetry magnetic signal and thus magnetic noise of some sort. Rather than filtering the noise signal and comparing it to some specified threshold, the sensing channel of the device itself is used to determine if the magnetic noise is of sufficient amplitude to affect the device's operation noting whether an increase in the sensing of intrinsic cardiac activity has occurred. If the increase in sensed intrinsic activity is time-correlated with the onset of the magnetic noise, the increased sensing can be assumed as most probably due to the device's sensing channel misinterpreting the magnetic noise as cardiac activity. The increased sensing of intrinsic cardiac activity may take the form of an increased measured intrinsic rate or the detection of a tachycardia. For example, the presence of EMI may be detected only if the monitored heart rate increases by a specified amount and for a specified duration, where the onset of the increase occurs nearly simultaneously with detection of a non-telemetry magnetic signal. While such noise is present, the device may enter a noise reversion mode which may include asynchronous pacing for bradycardia and/or inhibition of shock delivery. What follows is a description of an exemplary hardware platform for practicing the technique just described and a description of some specific embodiments.

1. Exemplary Implantable Device Description

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Cardiac rhythm management devices may also treat tachyarrhythmias, where the heart rate is too fast, by anti-tachycardia pacing and/or delivery of defibrillation shocks. Such devices are usually implanted subcutaneously in the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity.

The embodiment shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. The channels may be configured as either atrial or ventricular channels. In an example configuration, an atrial sensing/pacing channel includes ring electrode 43a and tip electrode 43b of bipolar lead 43c, sense amplifier 41, pulse generator 42, and a channel interface 40. A ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator 20 is also interfaced to the controller for delivering defibrillation shocks through electrodes selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing. The switch matrix 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels in order to control the delivery of paces in accordance with a pacing mode and/or deliver shock therapy in response to detection of a tachyarrhythmia such as ventricular fibrillation. The sensing circuitry of the device generates atrial and ventricular electrogram signals from the voltages sensed by the electrodes of a particular channel. An electrogram is analogous to a surface ECG and indicates the time course and amplitude of cardiac depolarization that occurs during either an intrinsic or paced beat. When an electrogram signal in an atrial or sensing channel exceeds a specified threshold, the controller detects an atrial or ventricular sense, respectively, which pacing algorithms may employ to trigger or inhibit pacing and from which heart rates may be derived by measuring the intervals between senses.

A telemetry interface 80 is also provided for enabling the controller to communicate with an external programmer via an inductive link between telemetry coil TC1 and a corresponding coil of the external programmer. The inductive link is an extremely short-range communications channel, the limiting factor on telemetry field strength being, not patient safety, but the ability of the sensing channels to inappropriately detect telemetry signals as sensed events. This necessarily means that when a time-varying magnetic field is strong enough to be detected by a sensing channel, it is also strong enough to be detected by the telemetry coil. As described below, the coil TC1 (or, optionally, a dedicated magnetic sensor MG1 as also shown in the figure) may thus be used to detect the presence of external time-varying magnetic fields that may constitute noise.

2. Exemplary Embodiments

As described above, certain anti-theft systems detect the presence of a magnetic tag placed on an article through the use of alternating magnetic fields. One such system in particular outputs a pulsed magnetic field at a 45 Hz rate with a 58 kHz carrier. The fields from this system will couple to the implanted leads of cardiac devices and can cause oversensing, either through demodulation of the high-frequency waveform by non-linearities in the sense amplifier input stage or through the low-frequency spectral content of the magnetic field itself. Although anti-theft magnetic fields and other EMI sources will couple to a telemetry coil, the coil (or other magnetic sensor) is electrically isolated from biopotentials such as cardiac electrical signals. The leads of an implanted device, on the other hand, are sensitive to both cardiac electrical activity and EMI. In accordance with the invention, information gathered from the telemetry subsystem of an implantable device is used to detect the presence of magnetic noise. If the detected noise is time-correlated with in an increase in sensed intrinsic cardiac activity, the latter may be presumed with high probability to be due to oversensing by the device's sensing channel caused by the presence of EMI.

The device may then be programmed to automatically enter a noise reversion mode which may include asynchronous pacing.

Figure 2:
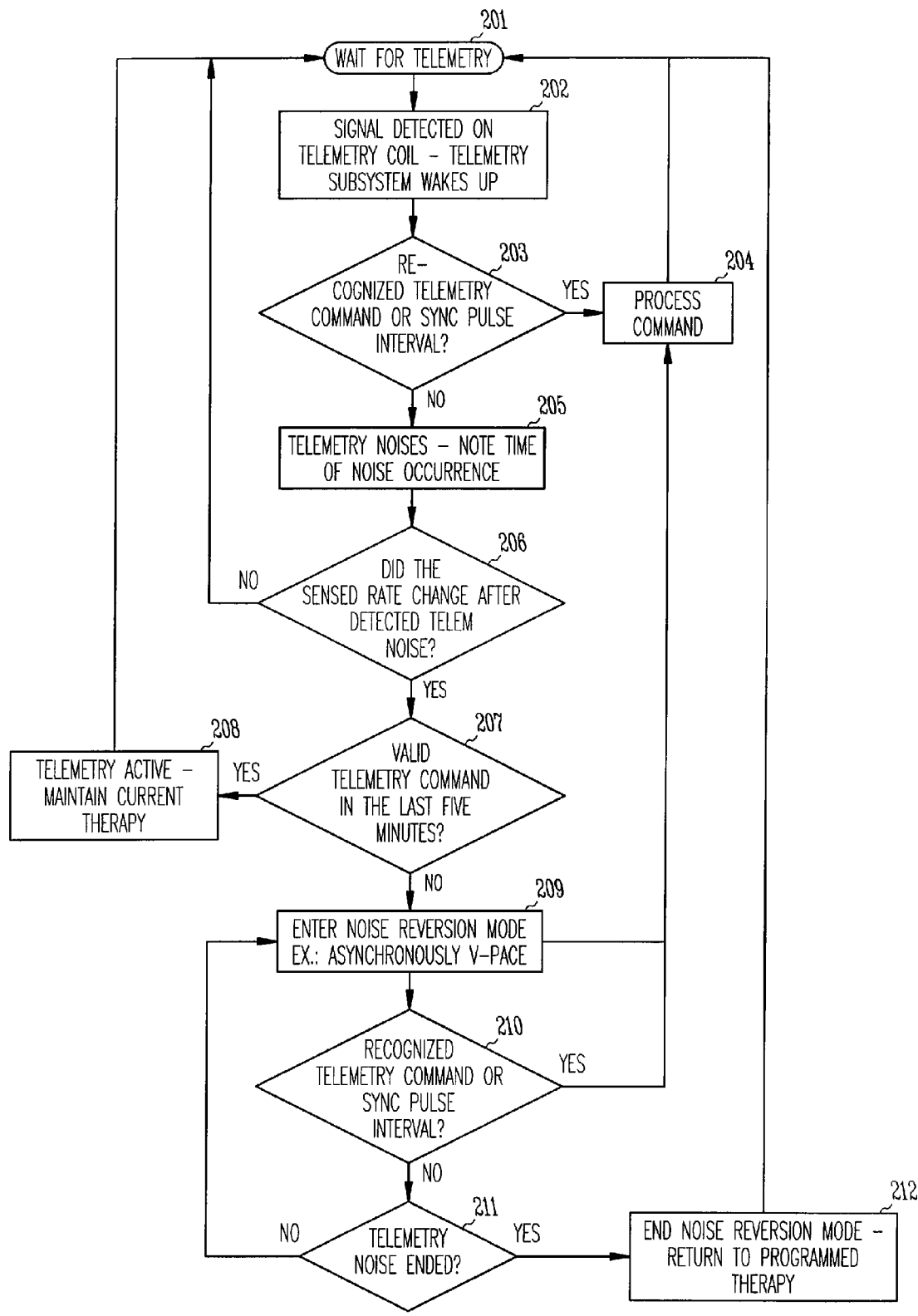
FIG. 2 illustrates a first embodiment of a method for detecting EMI.

FIG. 2 is a flowchart of a particular embodiment of the EMI detection technique as could be implemented in the programming of the device controller. The telemetry subsystem of device waits for a telemetry signal at step 201 and wakes up upon receipt of such a signal detected by the telemetry coil at step 202. If the signal is recognized as a valid telemetry command or occurs at a known sync pulse interval at step 203, the command (or sync pulse) is processed at step 204 and a return is made to the wait state 201. If the telemetry signal is not recognized, the signal is deemed to be magnetic noise coupled to the telemetry coil, either from EMI or the telemetry wand of the external programmer being out of range. The time of the noise occurrence is recorded at step 205. Next, at step 206, it is determined whether the sensed heart rate has increased at the same time at which the magnetic noise was detected. If not, the device returns to the wait state 201. If the increased sense rate and the noise signal are time-correlated, the device checks to see if a valid telemetry session was recently established (e.g., in the last 5 minutes) at step 207. This step is for safety reasons so that the device will not enter a noise reversion mode during telemetry sessions if communication is suddenly lost due to, for example, the telemetry wand of an external programmer falling off of the patient. If a telemetry session has been recently established, the device decides that telemetry is still active at step 208 and returns to the wait state 201. If no telemetry session has been recently established, the device enters a noise reversion mode at step 209, which may include asynchronous pacing and/or inhibition of defibrillation shocks. Once in the noise reversion mode, the device checks for valid telemetry signals at step 210 and for the disappearance of the noise at step 211. If a valid command or sync pulse is received, the command is processed at step 204 as the noise reversion mode is exited. If the telemetry noise has ended, the noise reversion mode is exited and the device returns to its normal programmed operation at step 212.

Figure 3:
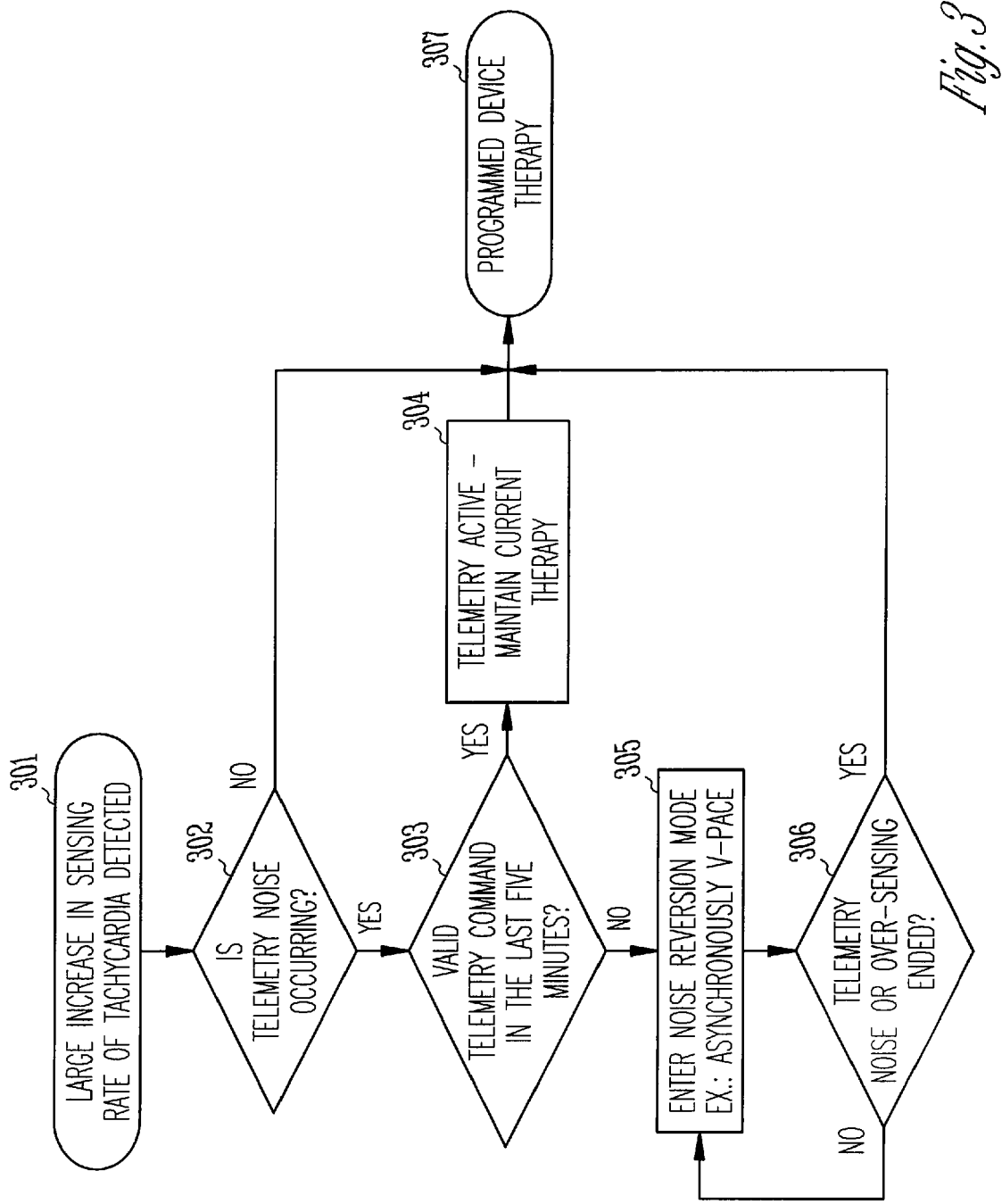
FIG. 3 illustrates a second embodiment of a method for detecting EMI.

FIG. 3 illustrates an alternative embodiment in which a subsystem of the device first waits for an increase in sensed heart rate of a specified magnitude to occur at step 301 and then checks for the presence of telemetry noise at step 302. If no noise is present, the device continues with programmed therapy at step 307. If telemetry noise is present but a valid telemetry command has been received in the last 5 minutes as determined at step 303, the device determines that telemetry is active at step 304 and proceeds to step 307 to continue programmed therapy. If no valid telemetry command has been received in the last 5 minutes and noise is present, the device enters the noise reversion mode at step 305. The device remains in the noise reversion mode until either telemetry noise or over-sensing has ended as determined at step 306. Because of the sporadic nature of tachycardia occurrences, this embodiment may provide a more efficient method to check for noise by only operating when therapy intervention may be required. In both embodiments, however, the end result is the same: a large increase in sensing rate triggers a noise reversion mode during periods of telemetry noise.

Figure 4:
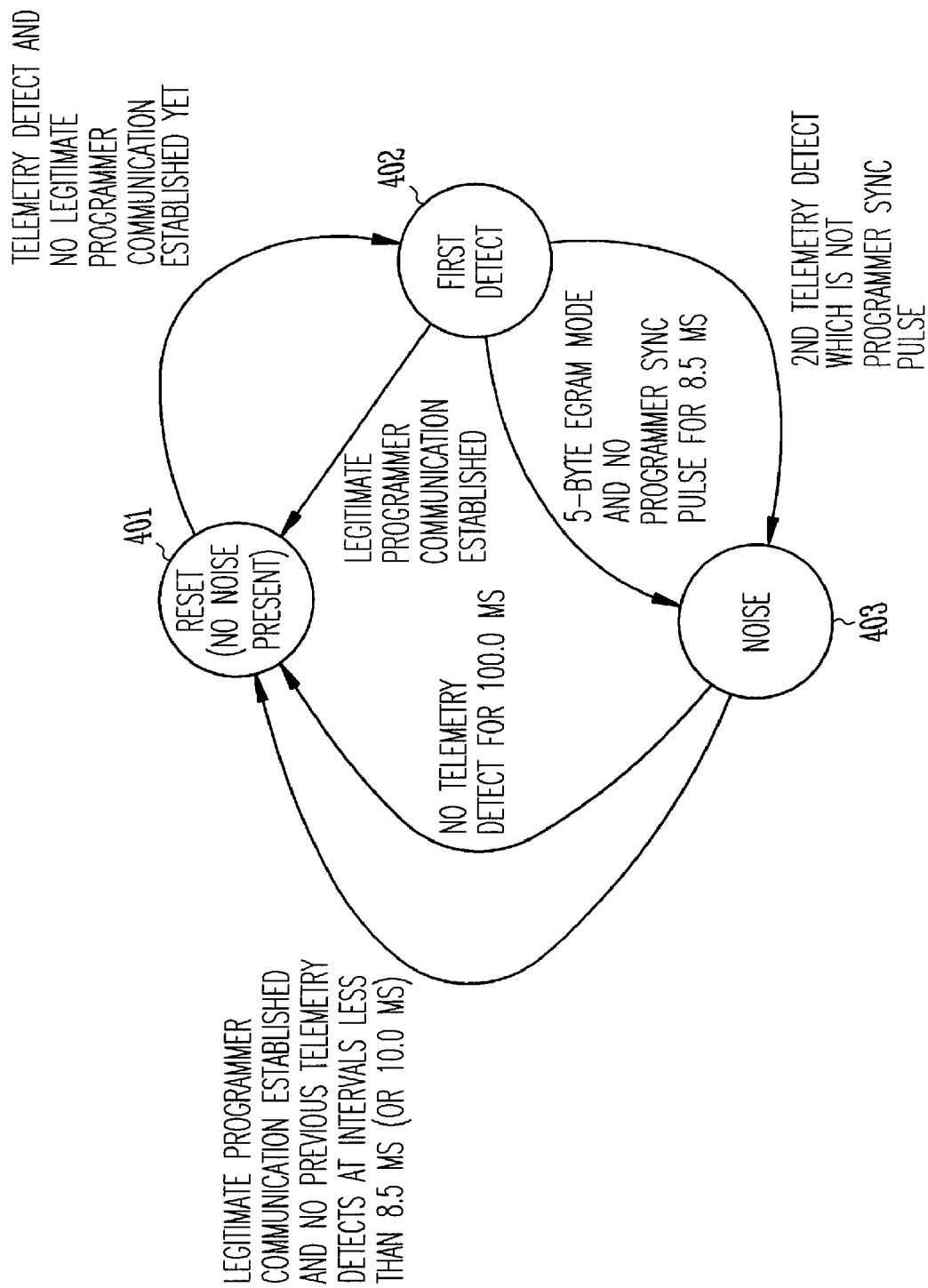
FIG. 4 illustrates an exemplary method for distinguishing magnetic noise from a telemetry signal.

Telemetry systems of implantable devices commonly employ a protocol to establish two-way communications between an implanted device and an external programmer in which regularly spaced magnetic field pulses function to synchronize the communications link. Such "sync" pulses are generated by the external programmer at a specified interval. In one particular implementation, sync pulses are generated at 8.333 ms. All subsequent commands or data are sent during specified transmission windows between the sync pulses. A state machine type of algorithm as illustrated in FIG. 4 may be employed to distinguish between EMI signals and programmer-generated sync pulses. The state machines begins in its reset state 401 indicating that either the telemetry system has been reset or sync pulses are currently being received. If programmer communication has not previously been established and a magnetic field pulse is received, the state machine enters its first detect state 402. If a subsequent magnetic field pulse is received at an interval shorter than 8.333 ms, the state machine enters its noise state 403 indicating that EMI pulses are being received at intervals shorter than expected. The state machine also enters its noise state 403 if a magnetic field pulse is received at an interval longer than 8.333 ms. The state machine will remain in the noise state 403 as long as magnetic field pulses are received at intervals other than 8.333 ms, and a telemetry noise flag may be raised while the state machine is in the noise state. If programmer communication is established and no previous pulses have been detected at intervals less than 8.333 ms, the state machine returns to the reset state 401. The state machine also returns to the reset state if no magnetic pulses have been received for a specified time-out interval (e.g., 100 ms).

Figure 5:
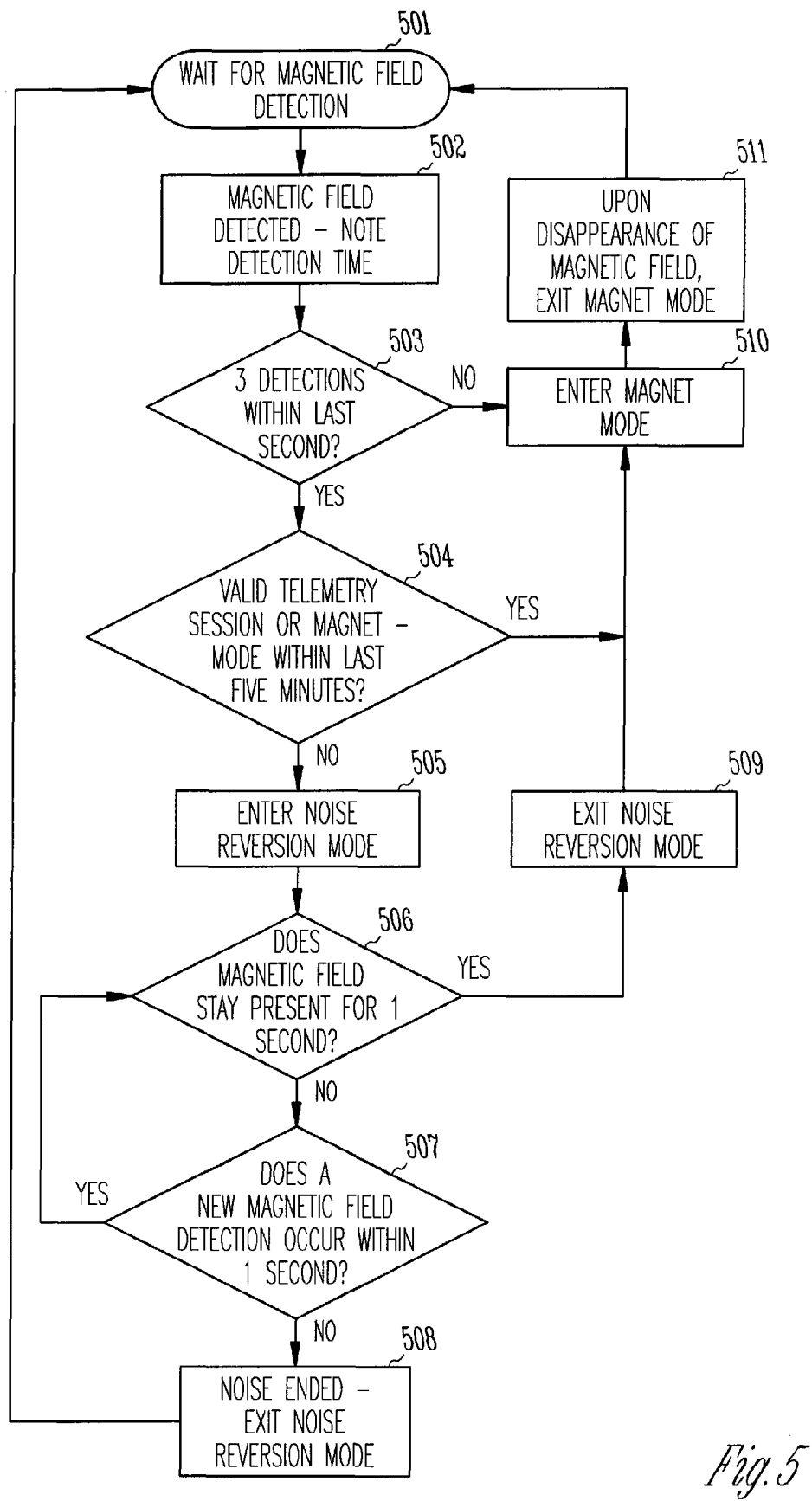
FIG. 5 illustrates a third embodiment of a method for detecting EMI.

Certain implantable devices utilize magnetic sensor such as a reed switch or Hall-effect sensor for enabling a safety or other type of mode when a magnet is placed near the device. Such a "magnet mode" is entered by the device when the static magnetic field of the magnet closes the reed switch or creates a significant voltage across the Hall-effect sensor. Because the magnetic field which triggers the magnet mode is steady, the same sensor used to detect the presence of a magnet can also be used to detect alternating magnetic fields and trigger a noise reversion mode. FIG. 5 illustrates an alternative embodiment of an EMI detection algorithm which utilizes the magnetic sensor used to trigger a magnet mode for also detecting magnetic noise. The device waits for detection of a magnetic field at step 501. Following detection of a signal on the magnetic sensor at step 502, the device determines whether a steady or alternating magnetic field is present by checking if three detections have occurred within the past second at step 503. If not, the device enters the magnet mode at step 510, which is exited upon disappearance of the magnetic field at step 511. A detected alternating magnetic field, on the other hand, indicates the presence of magnetic noise. Before entering the noise reversion mode at step 505, the device first checks at step 504 if a valid telemetry session or magnet mode has been recently established. This prevents the device inadvertently entering the noise reversion mode during an implant or follow-up session. Once in noise reversion mode, the device continues to monitor the magnetic noise at steps 506 and 507. If the magnetic field becomes steady, the device exits the noise reversion mode and enters the magnet mode. If the field disappears, the device exits the noise reversion mode at steps 508 or 509 and waits for the next magnetic field detection.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for operating an implantable cardiac device in order to detect a presence of electromagnetic interference (EMI), comprising:

monitoring a heart rate via a sensing channel which incorporates an implanted lead;

upon detecting an increase in heart rate by a specified amount, monitoring for a detection of a magnetic signal with a magnetic sensor;

determining whether the detected magnetic signal is a magnetic noise signal or a valid telemetry signal; and, detecting the presence of EMI if no said valid telemetry signal has been received within a specified prior time period.

2. The method of claim 1 further comprising entering a noise reversion mode upon detection of EMI.

3. The method of claim 2 further comprising exiting the noise reversion mode upon receipt of the valid telemetry signal.

4. The method of claim 2 further comprising monitoring for the presence of a magnetic signal in the noise reversion mode and exiting the noise reversion mode after the EMI has disappeared.

5. The method of claim 2 wherein the noise reversion mode includes asynchronous pacing.

6. The method of claim 2 wherein the noise reversion mode includes inhibition of defibrillation shocks.

7. The method of claim 1 wherein the magnetic signal is determined to be the telemetry signal if the magnetic signal is recognized as either a valid telemetry command or a sync pulse.

8. The method of claim 1 wherein the magnetic sensor is a telemetry coil.

9. The method of claim 1 wherein the magnetic sensor is normally used by the device to detect a static magnetic field.

10. The method of claim 9 further comprising detecting the magnetic signal only if alternating detections occur within a specified time period, indicating a time varying magnetic field.

11. An implantable cardiac device configured to detect a presence of electromagnetic interference (EMI), comprising:
a sensing channel which incorporates an implantable lead for sensing cardiac electrical activity;
a magnetic sensor;
a controller interfaced to the sensing channel and the magnetic sensor;
wherein the controller is programmed to monitor heart rate via the sensing channel and, upon detecting an increase in heart rate by a specified amount, monitoring for a detection of a magnetic signal via the magnetic sensor; and,
wherein the controller is further programmed to determine whether the detected magnetic signal is a magnetic noise signal or a valid telemetry signal and to detect the presence of EMI if no said valid telemetry signal has been received within a specified prior time period.

12. The device of claim 11 wherein the controller is further programmed to enter a noise reversion mode upon detection of EMI.

13. The device of claim 12 wherein the controller is further programmed to exit the noise reversion mode upon receipt of the valid telemetry signal.

14. The device of claim 12 wherein the controller is further programmed to monitor for the presence of a magnetic signal in the noise reversion mode and exit the noise reversion mode after the EMI has disappeared.

15. The device of claim 12 wherein the noise reversion mode includes asynchronous pacing.

16. The device of claim 12 wherein the noise reversion mode includes inhibition of defibrillation shocks.

17. The device of claim 11 wherein the controller is further programmed to determine the magnetic signal to be the telemetry signal if the magnetic signal is recognized as either a valid telemetry command or a sync pulse.

18. The device of claim 11 wherein the magnetic sensor is a telemetry coil.

19. The device of claim 11 wherein the magnetic sensor is normally used by the device to detect a static magnetic field.

20. The device of claim 19 wherein the controller is further programmed to detect the magnetic signal only if alternating detections occur within a specified time period, indicating a time varying magnetic field.

* * * * *